US010499917B2

(12) United States Patent
Scheib et al.

(10) Patent No.: US 10,499,917 B2
(45) Date of Patent: Dec. 10, 2019

(54) SURGICAL STAPLER END EFFECTOR WITH KNIFE POSITION INDICATORS

(71) Applicant: Ethicon Endo-Surgery, LLC, Guaynabo, PR (US)

(72) Inventors: Charles J. Scheib, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 463 days.

(21) Appl. No.: 14/884,228

(22) Filed: Oct. 15, 2015

(65) Prior Publication Data

US 2017/0105732 A1    Apr. 20, 2017

(51) Int. Cl.
*A61B 17/10* (2006.01)
*A61B 17/068* (2006.01)
(Continued)

(52) U.S. Cl.
CPC .......... *A61B 17/105* (2013.01); *A61B 17/068* (2013.01); *A61B 17/07207* (2013.01);
(Continued)

(58) Field of Classification Search
CPC .............. A61B 17/068; A61B 17/105; A61B 2090/0811; A61B 2090/0804; A61B 17/07207
(Continued)

(56) References Cited

U.S. PATENT DOCUMENTS 2,224,461 A * 12/1940 Solomon ................. F16B 15/08
206/340
4,319,576 A    3/1982 Rothfuss
(Continued)

FOREIGN PATENT DOCUMENTS

CN    202 313 537 U    7/2012
CN    202 982 106 U    6/2013
(Continued)

OTHER PUBLICATIONS

U.S. Appl. No. 14/810,786, filed Jul. 29, 2015.
(Continued)

*Primary Examiner* — Andrew M Tecco
*Assistant Examiner* — Nicholas E Igbokwe
(74) *Attorney, Agent, or Firm* — Frost Brown Todd LLC

(57) ABSTRACT

A surgical instrument includes an end effector. The end effector includes a first jaw, a second jaw, and a translating member. The first jaw includes an anvil, an upper elongated channel extending therethrough, and a first plurality of indicia positioned proximate to the first elongated channel. The second jaw includes a second elongated channel extending therethrough and a second plurality of indicia positioned proximate to the second elongated channel. The translating member is received within the first and second channels. The translating member is configured to slide distally along the first and second channels and engage a wedge sled for forming staples. The translating member includes a first indicator and a second indicator, wherein the first and second indicators in conjunction with the first and lower plurality of indicia are respectively configured to indicate one or both of staple usage or a cut position to an operator.

20 Claims, 16 Drawing Sheets

(51) Int. Cl.
  *A61B 17/072* (2006.01)
  *A61B 90/00* (2016.01)
(52) U.S. Cl.
  CPC .............. *A61B 2017/07257* (2013.01); *A61B 2017/07271* (2013.01); *A61B 2017/07285* (2013.01); *A61B 2090/0804* (2016.02); *A61B 2090/0811* (2016.02)
(58) Field of Classification Search
  USPC .................................................. 227/19, 177.1
  See application file for complete search history.

(56) References Cited

U.S. PATENT DOCUMENTS

| | | | |
|---|---|---|---|
| 4,805,823 A | 2/1989 | Rothfuss | |
| 4,925,082 A * | 5/1990 | Kim .................. | B25C 5/025 206/340 |
| 5,040,715 A | 8/1991 | Green et al. | |
| 5,156,315 A | 10/1992 | Green et al. | |
| 5,282,807 A | 2/1994 | Knoepfler | |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,364,001 A | 11/1994 | Bryan | |
| 5,364,003 A | 11/1994 | Williamson, IV et al. | |
| 5,389,098 A | 2/1995 | Truruta et al. | |
| 5,397,324 A | 3/1995 | Carroll et al. | |
| 5,403,312 A | 4/1995 | Yates et al. | |
| 5,415,334 A | 5/1995 | Williamson et al. | |
| 5,417,361 A | 5/1995 | Williamson et al. | |
| 5,427,298 A * | 6/1995 | Tegtmeier ............ | B25C 5/1689 173/20 |
| 5,452,837 A | 9/1995 | Williamson, IV et al. | |
| 5,465,895 A | 11/1995 | Knodel et al. | |
| 5,551,622 A | 9/1996 | Yoon | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,709,335 A | 1/1998 | Heck | |
| 5,752,644 A | 5/1998 | Bolanos et al. | |
| 5,792,135 A | 8/1998 | Madhani et al. | |
| 5,814,055 A | 9/1998 | Knodel et al. | |
| 5,816,471 A | 10/1998 | Plyley et al. | |
| 5,817,084 A | 10/1998 | Jensen | |
| 5,878,193 A | 3/1999 | Wang et al. | |
| 6,003,517 A | 12/1999 | Sheffield et al. | |
| 6,079,606 A | 6/2000 | Milliman et al. | |
| 6,231,565 B1 | 5/2001 | Tovey et al. | |
| 6,264,089 B1 | 7/2001 | Hasegawa et al. | |
| 6,364,888 B1 | 4/2002 | Niemeyer et al. | |
| 6,443,970 B1 | 9/2002 | Schulze et al. | |
| 6,669,073 B2 | 12/2003 | Milliman et al. | |
| 6,694,984 B2 | 2/2004 | Habib | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,235,089 B1 | 6/2007 | McGuckin, Jr. | |
| 7,237,708 B1 * | 7/2007 | Guy .................... | A61B 17/072 227/175.1 |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,434,717 B2 | 10/2008 | Shelton, IV et al. | |
| 7,524,320 B2 | 4/2009 | Tierney et al. | |
| 7,635,074 B2 | 12/2009 | Olson et al. | |
| 7,641,091 B2 | 1/2010 | Olson et al. | |
| 7,651,017 B2 | 1/2010 | Ortiz et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 7,963,433 B2 | 6/2011 | Whitman et al. | |
| 7,980,443 B2 | 7/2011 | Scheib et al. | |
| 7,988,028 B2 | 8/2011 | Farascioni et al. | |
| 8,011,555 B2 | 9/2011 | Tarinelli et al. | |
| 8,012,170 B2 | 9/2011 | Whitman et al. | |
| 8,210,411 B2 | 7/2012 | Yates et al. | |
| 8,342,377 B2 | 1/2013 | Milliman et al. | |
| 8,360,298 B2 | 1/2013 | Farascioni et al. | |
| 8,393,516 B2 | 3/2013 | Kostrzewski | |
| 8,408,439 B2 | 4/2013 | Huang et al. | |
| 8,418,908 B1 | 4/2013 | Beardsley | |
| 8,453,914 B2 | 6/2013 | Laurent et al. | |
| 8,479,969 B2 | 7/2013 | Shelton, IV | |
| 8,485,412 B2 | 7/2013 | Shelton, IV et al. | |
| 8,496,153 B2 | 7/2013 | Demmy et al. | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,708,213 B2 | 4/2014 | Shelton, IV et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,833,632 B2 | 9/2014 | Swensgard | |
| 8,844,789 B2 | 9/2014 | Shelton, IV et al. | |
| 8,931,679 B2 | 1/2015 | Kostrzewski | |
| 8,940,000 B2 | 1/2015 | Kasvikis et al. | |
| 9,050,084 B2 | 6/2015 | Schmid et al. | |
| 9,186,142 B2 | 11/2015 | Fanelli et al. | |
| 9,237,890 B2 | 1/2016 | Kostrzewski | |
| 9,272,406 B2 | 3/2016 | Aronhalt et al. | |
| 9,301,759 B2 | 4/2016 | Spivey et al. | |
| 9,386,984 B2 | 7/2016 | Aronhalt et al. | |
| 9,402,628 B2 | 8/2016 | Beardsley | |
| 9,492,146 B2 | 11/2016 | Kostrzewski et al. | |
| 9,498,215 B2 | 11/2016 | Duque et al. | |
| 9,517,065 B2 | 12/2016 | Simms et al. | |
| 9,572,577 B2 | 2/2017 | Lloyd et al. | |
| 9,615,826 B2 | 4/2017 | Shelton, IV et al. | |
| 9,706,999 B2 | 7/2017 | Motai | |
| 9,724,091 B2 | 8/2017 | Shelton, IV et al. | |
| 9,750,502 B2 | 9/2017 | Scirica et al. | |
| 9,775,613 B2 | 10/2017 | Shelton, IV et al. | |
| 9,801,627 B2 | 10/2017 | Harris et al. | |
| 9,827,002 B2 | 11/2017 | Hausen et al. | |
| 2008/0169328 A1 | 7/2008 | Shelton, IV | |
| 2008/0169332 A1 | 7/2008 | Shelton, IV et al. | |
| 2009/0048589 A1 | 2/2009 | Takashino et al. | |
| 2009/0114701 A1 * | 5/2009 | Zemlok ............... | A01H 5/0222 227/176.1 |
| 2009/0206131 A1 | 8/2009 | Weisenburgh, II et al. | |
| 2009/0206144 A1 * | 8/2009 | Doll .................. | A61B 17/07207 227/177.1 |
| 2010/0069942 A1 * | 3/2010 | Shelton, IV ...... | A61B 17/07207 606/170 |
| 2011/0036891 A1 * | 2/2011 | Zemlok ............ | A61B 17/07207 227/176.1 |
| 2012/0111920 A1 * | 5/2012 | Kostrzewski .... | A61B 17/07207 227/176.1 |
| 2013/0168431 A1 * | 7/2013 | Zemlok ............ | A61B 17/07207 227/175.1 |
| 2013/0334284 A1 | 12/2013 | Swayze | |
| 2014/0081176 A1 | 3/2014 | Hassan | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0299648 A1 | 10/2014 | Shelton, IV et al. | |
| 2015/0108198 A1 | 4/2015 | Estrella | |
| 2015/0150620 A1 | 6/2015 | Miyamoto et al. | |
| 2015/0272575 A1 | 10/2015 | Leimbach et al. | |
| 2015/0374360 A1 | 12/2015 | Scheib et al. | |
| 2015/0374373 A1 | 12/2015 | Rector et al. | |
| 2017/0105725 A1 | 4/2017 | Scheib et al. | |

(56) References Cited

U.S. PATENT DOCUMENTS

| | | | |
|---|---|---|---|
| 2017/0105727 | A1 | 4/2017 | Scheib et al. |
| 2017/0105728 | A1 | 4/2017 | Scheib et al. |
| 2017/0105729 | A1 | 4/2017 | Scheib et al. |
| 2017/0105730 | A1 | 4/2017 | Scheib et al. |
| 2017/0105731 | A1 | 4/2017 | Scheib et al. |
| 2017/0105733 | A1 | 4/2017 | Scheib et al. |

FOREIGN PATENT DOCUMENTS

| | | |
|---|---|---|
| CN | 204 158 440 U | 2/2015 |
| CN | 204 158 441 U | 2/2018 |
| EP | 0 623 311 A2 | 11/1994 |
| EP | 0 878 169 A1 | 11/1998 |
| EP | 1 790 293 A2 | 5/2007 |
| EP | 2 090 255 A1 | 8/2009 |
| EP | 2 098 170 A2 | 9/2009 |
| EP | 2 283 779 A1 | 2/2011 |
| EP | 2 386 253 A2 | 11/2011 |
| EP | 2 583 630 A2 | 4/2013 |
| EP | 2 586 379 A1 | 5/2013 |
| EP | 2 886 070 A1 | 6/2015 |
| WO | WO 94/24943 A1 | 11/1994 |
| WO | WO 96/18344 A2 | 6/1996 |
| WO | WO 2009/022614 A1 | 2/2009 |
| WO | WO 2012/141679 A1 | 10/2012 |
| WO | WO 2013/019445 A2 | 7/2013 |
| WO | WO 2015/137181 A1 | 9/2015 |
| WO | WO 2015/153324 A1 | 10/2015 |

OTHER PUBLICATIONS

Gumbs, A., et al., "Laparoscopic liver resection: when to use the laparoscopic stapler device," HPB, 2008, 10:296-303, 8 pgs.

Rahbari, N.N., et al., "Randomized clinical trial of stapler versus transection in elective liver resection," British Journal of Surgery, 2014, 101:200-207, 8 pgs.

Schemmer, P., et al., "Liver transection using vascular stapler: A review", HPB, 2008, 10:249-252, 4 pgs.

US FDA 510K Application #K061095 for Endo GIA Stapler, indicated transection/resection of liver substance, hepatic vasculature, and biliary structures, May 31, 2006, 121 pgs.

European Search Report and Written Opinion dated Mar. 17, 2017 for Application No. EP 16193980.6, 6 pgs.

European Search Report and Written Opinion dated Jan. 13, 2017 for Application No. EP 16193975.6, 9 pgs.

European Search Report and Written Opinion dated Jan. 16, 2017 for Application No. EP 16193965.7, 8 pgs.

European Search Report and Written Opinion dated Jan. 13, 2017 for Application No. EP 16193976.4, 9 pgs.

European Search Report and Written Opinion dated Mar. 14, 2017 for Application No. EP 16193957.4, 6 pgs.

European Search Report and Written Opinion dated Feb. 8, 2017 for Application No. EP 16193964.1, 7 pgs.

European Search Report, Partial, and Written Opinion dated Feb. 22, 2017 for Application No. EP 16193954.1, 9 pgs.

European Search Report and Written Opinion dated Aug. 11, 2017 for Application No. EP 16193954.1, 24 pgs.

Declaration of Non-Establishment of International Search Report dated Mar. 10, 2017 for Application No. PCT/US2016/055880, 6 pgs.

International Search Report and Written Opinion dated Jan. 3, 2017 for Application No. PCT/US2016/055872, 9 pgs.

International Search Report and Written Opinion dated Jan. 4, 2017 for Application No. PCT/US2016/056757, 13 pgs.

International Search Report and Written Opinion dated Jan. 16, 2017 for Application No. PCT/US2016/055874, 10 pgs.

International Search Report and Written Opinion dated Jan. 16, 2017 for Application No. PCT/US2016/055877, 13 pgs.

International Search Report and Written Opinion dated Jan. 2, 2017 for Application No. PCT/US2016/055878, 9 pgs.

International Search Report and Written Opinion dated Mar. 8, 2017 for Application No. PCT/US2016/056756, 10 pgs.

International Search Report and Written Opinion dated Apr. 9, 2018 for Application No. PCT/US2016/056754, 28 pgs.

* cited by examiner

SURGICAL STAPLER END EFFECTOR WITH KNIFE POSITION INDICATORS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. patent application Ser. No. 14/810,786, entitled "Surgical Staple Cartridge with Compression Feature at Knife Slot," filed Jul. 29, 2015, issued as U.S. Pat. No. 10,314,580 on Jun. 11, 2019; U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,379 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as 9,808,248 on Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodi

Figure 1:
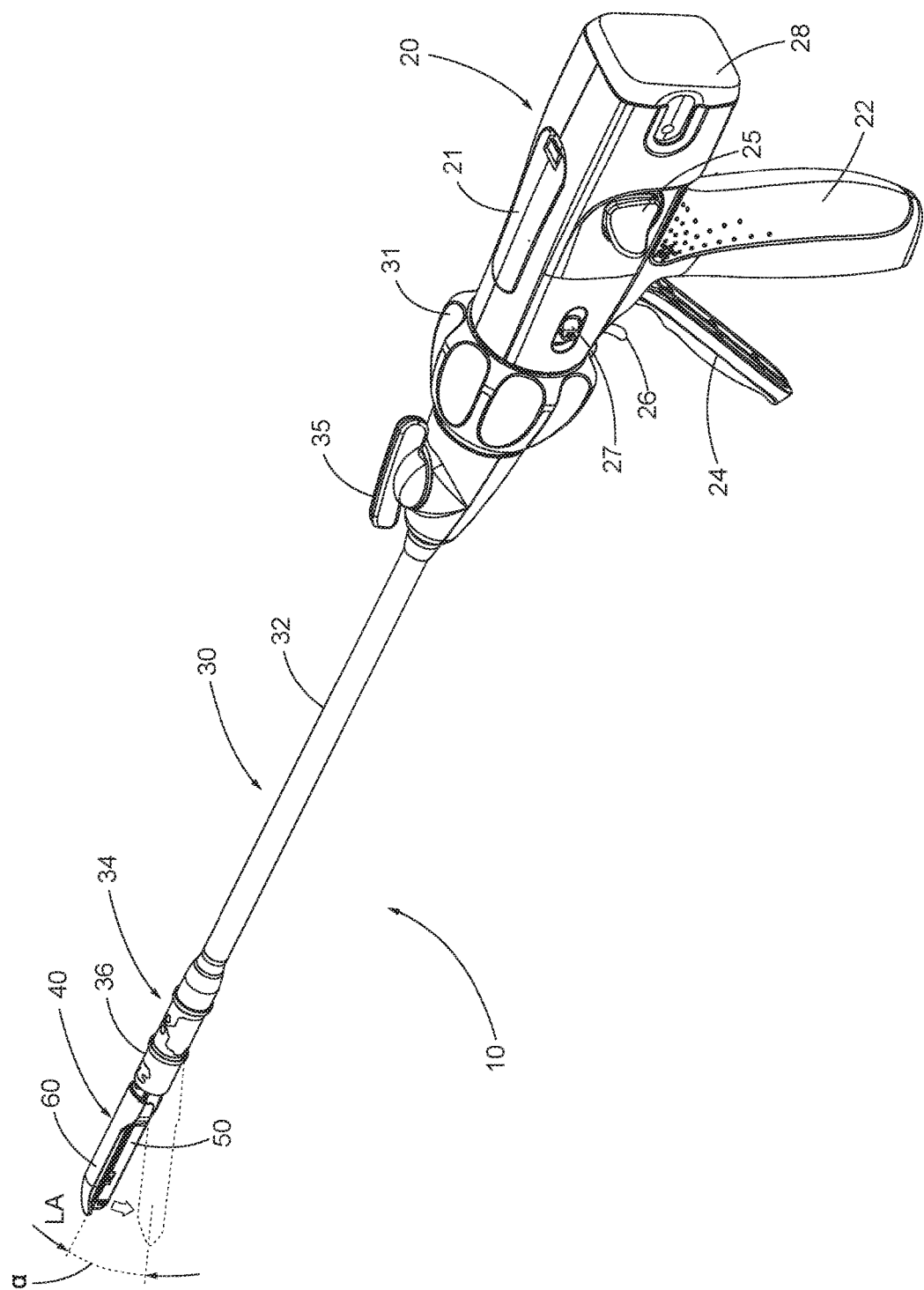
- FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
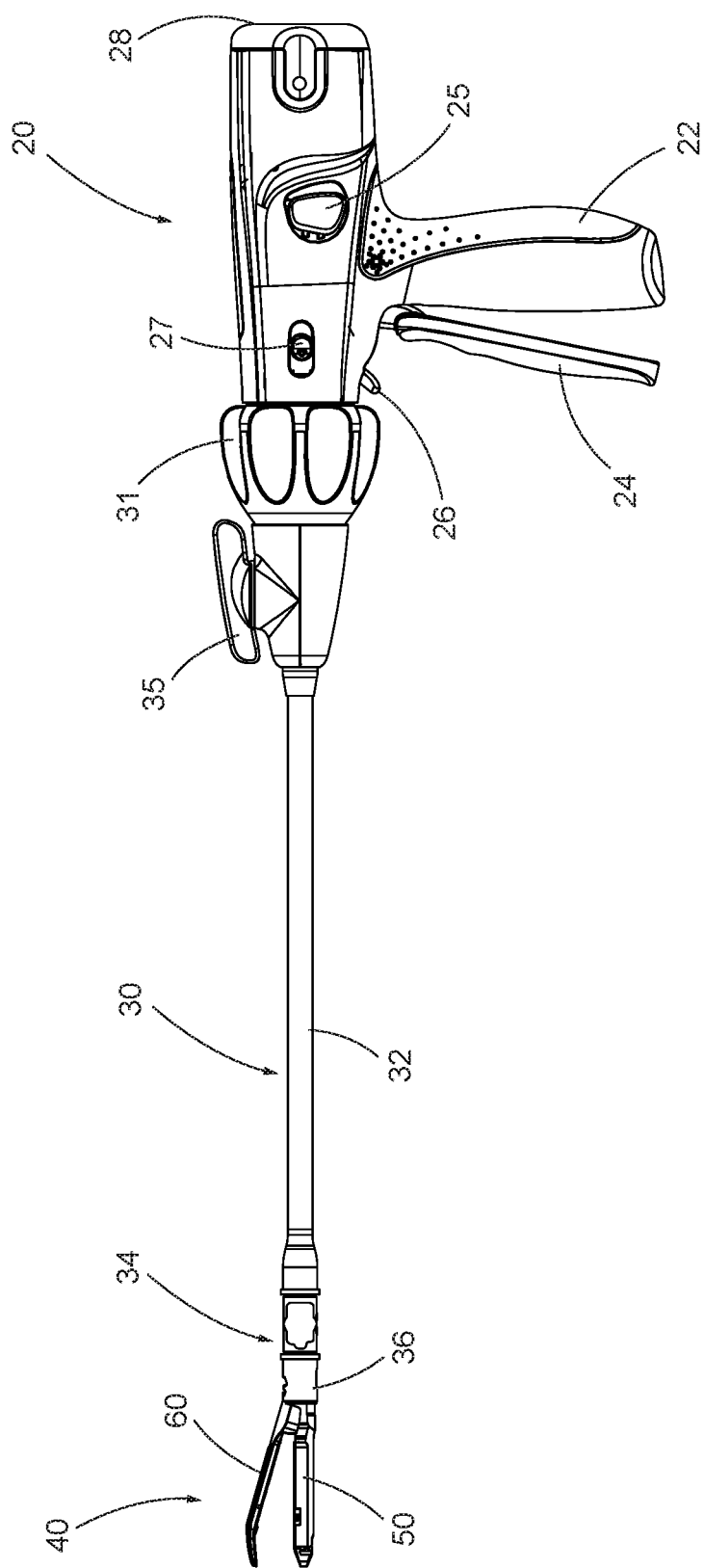
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
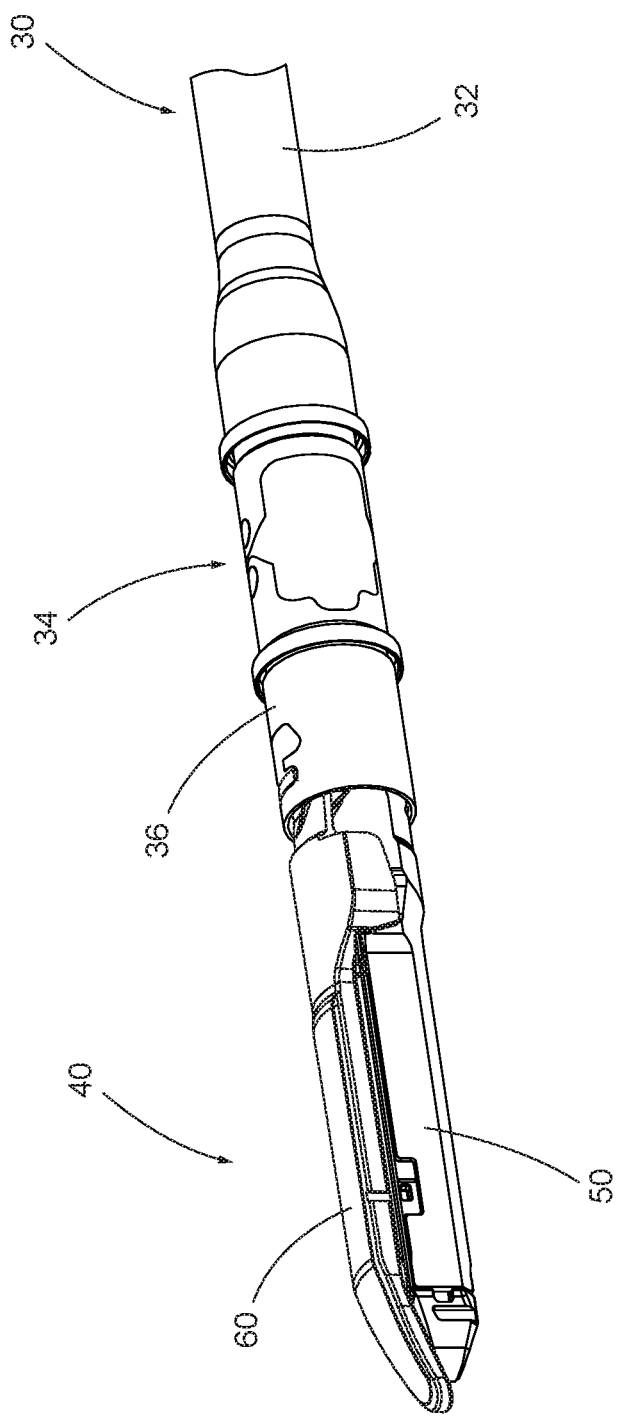
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. Pat. App. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 4:
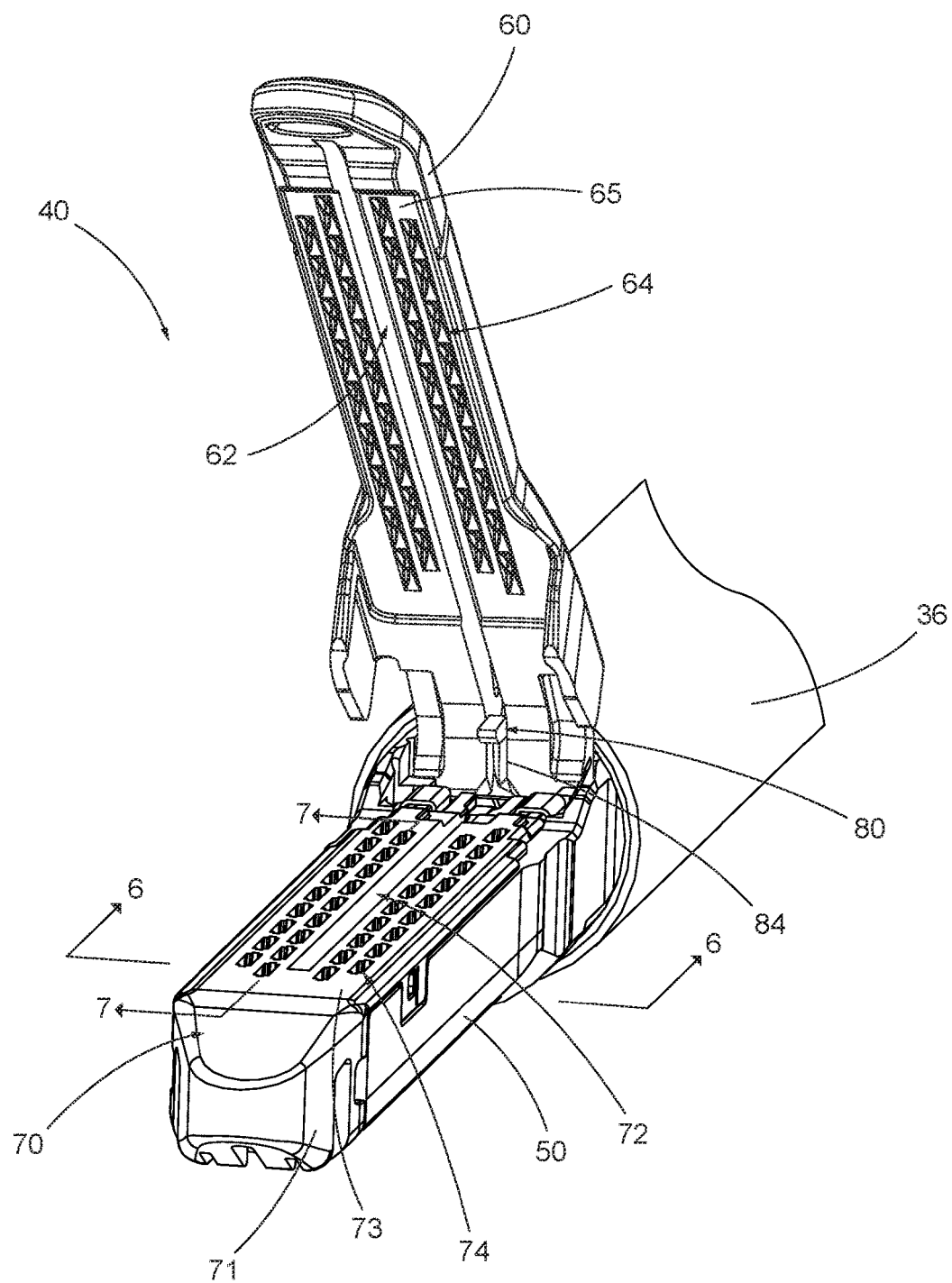
FIG. 4 depicts a perspective view of the end effector of FIG. 3, with the end effector in an open configuration.
Figure 5:
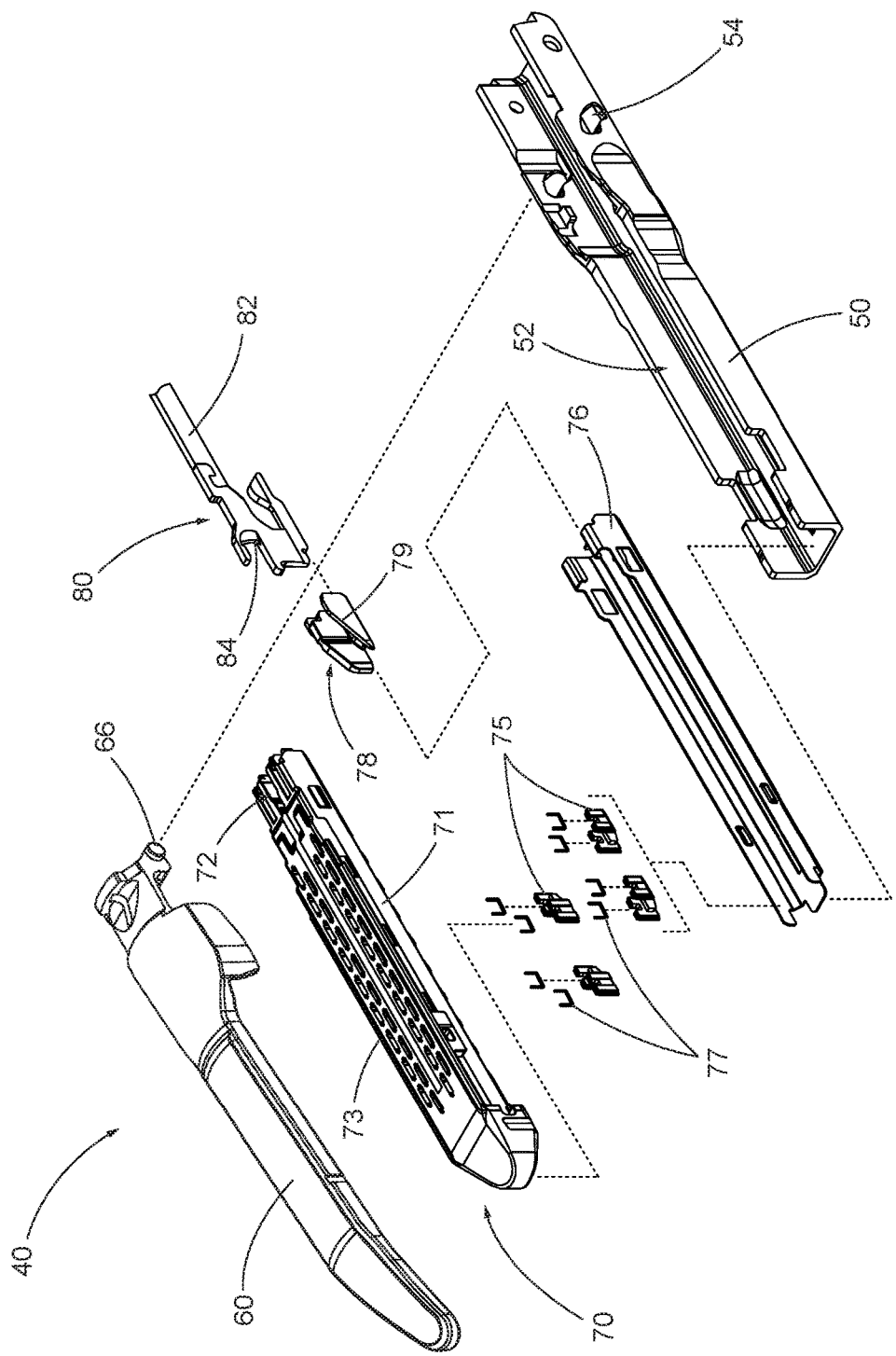
FIG. 5 depicts an exploded perspective view of the end effector of FIG. 3.

As also shown in FIGS. 3-5, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,898,248 on Nov. 7, 2017, the disclosure of which is incorporated by reference herein. Other suitable forms that lower jaw (50) may take will be apparent to those of ordinary skill in the art in view of the teachings herein.

Figure 6:
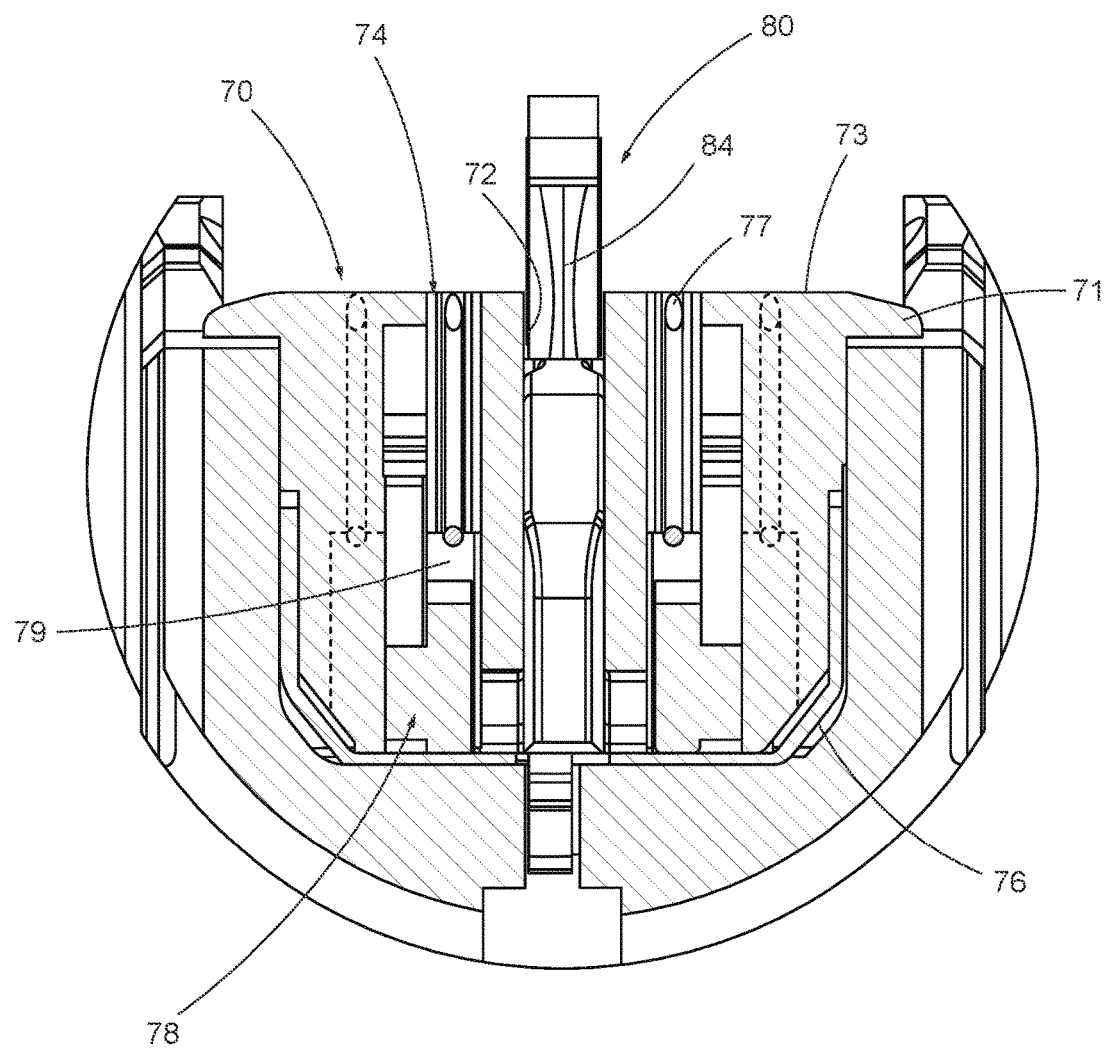
FIG. 6 depicts a cross-sectional end view of the end effector of FIG. 3, taken along line 6-6 of FIG. 4.
Figure 7A:
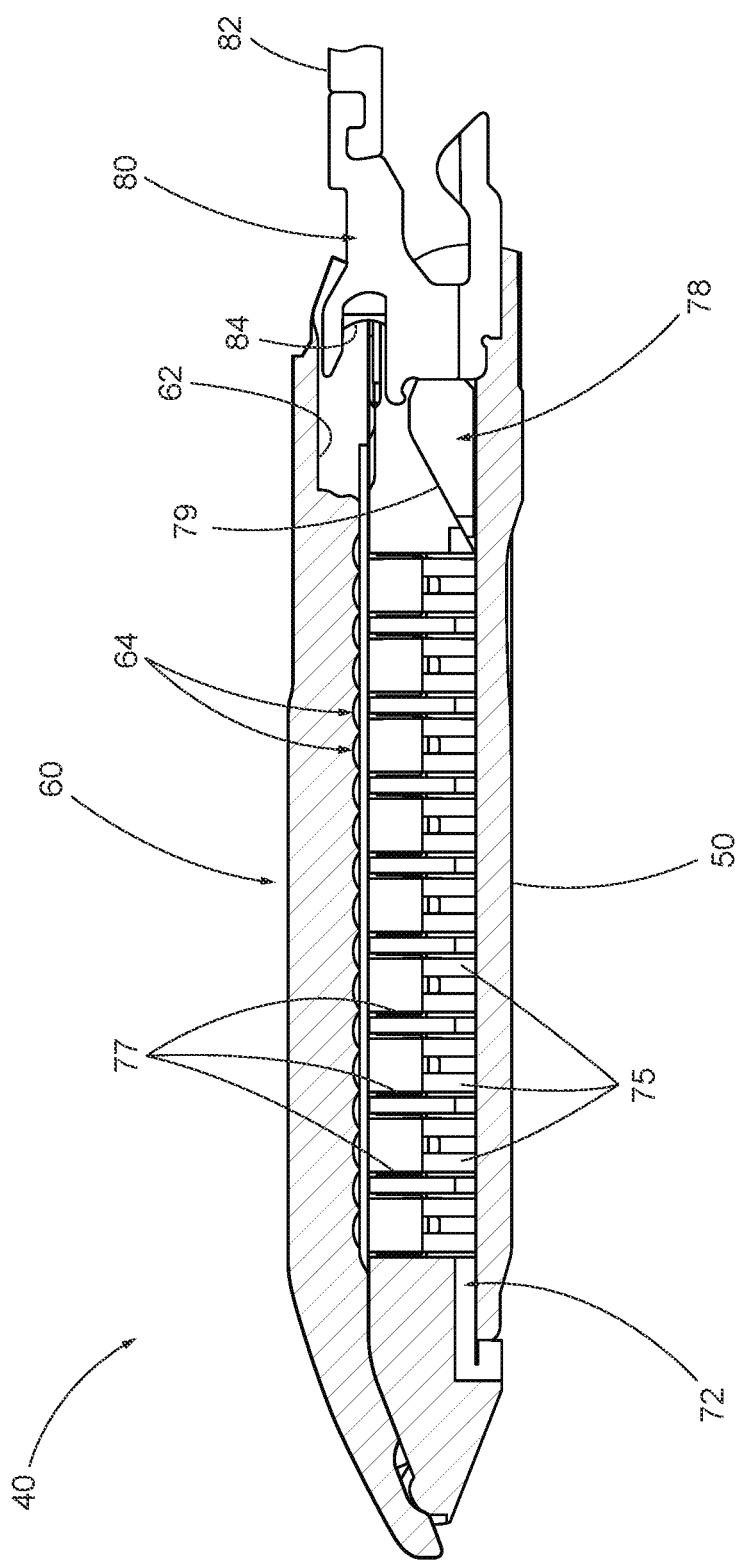
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,715,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
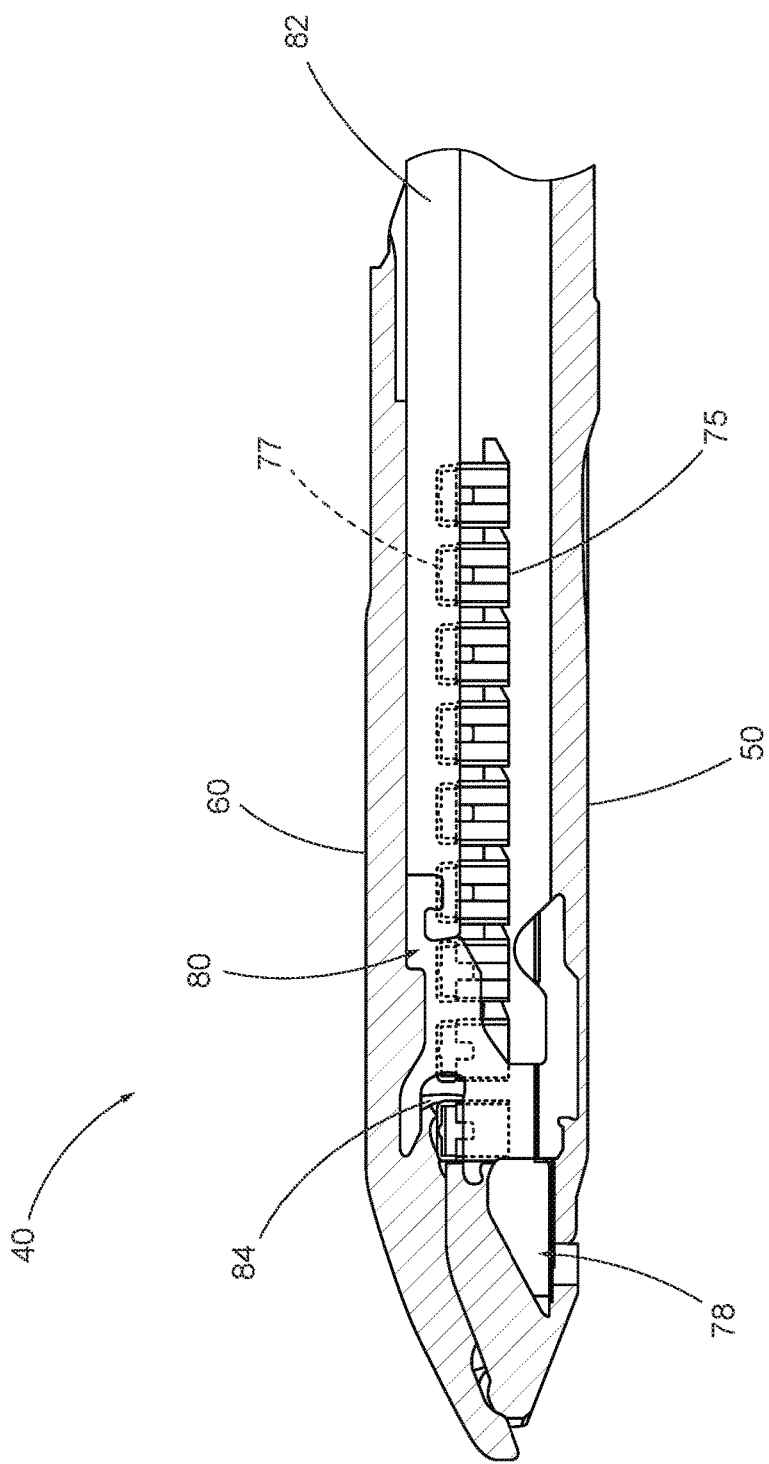
FIG. 7B depicts a cross-sectional side view of the end effector of FIG. 3, taken along line 7-7 of FIG. 4, with the firing beam in a distal position.

In the present example, knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; and/or at least some of the teachings of U.S. patent application Ser. No. 14/314,108, entitled "Method of Using Lockout Features for Surgical Staple cartridge," filed on Jun. 25, 2014, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, issued as U.S. Pat. No. 10,335,147 on Jul. 2, 2019, the disclosure of which is incorporated by reference herein. Exemplary features that may be used to provide longitudinal translation of closure ring (36) relative to end effector (40) will be described in greater detail below.

As noted above, handle assembly (20) includes pistol grip (22) and closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of closure trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
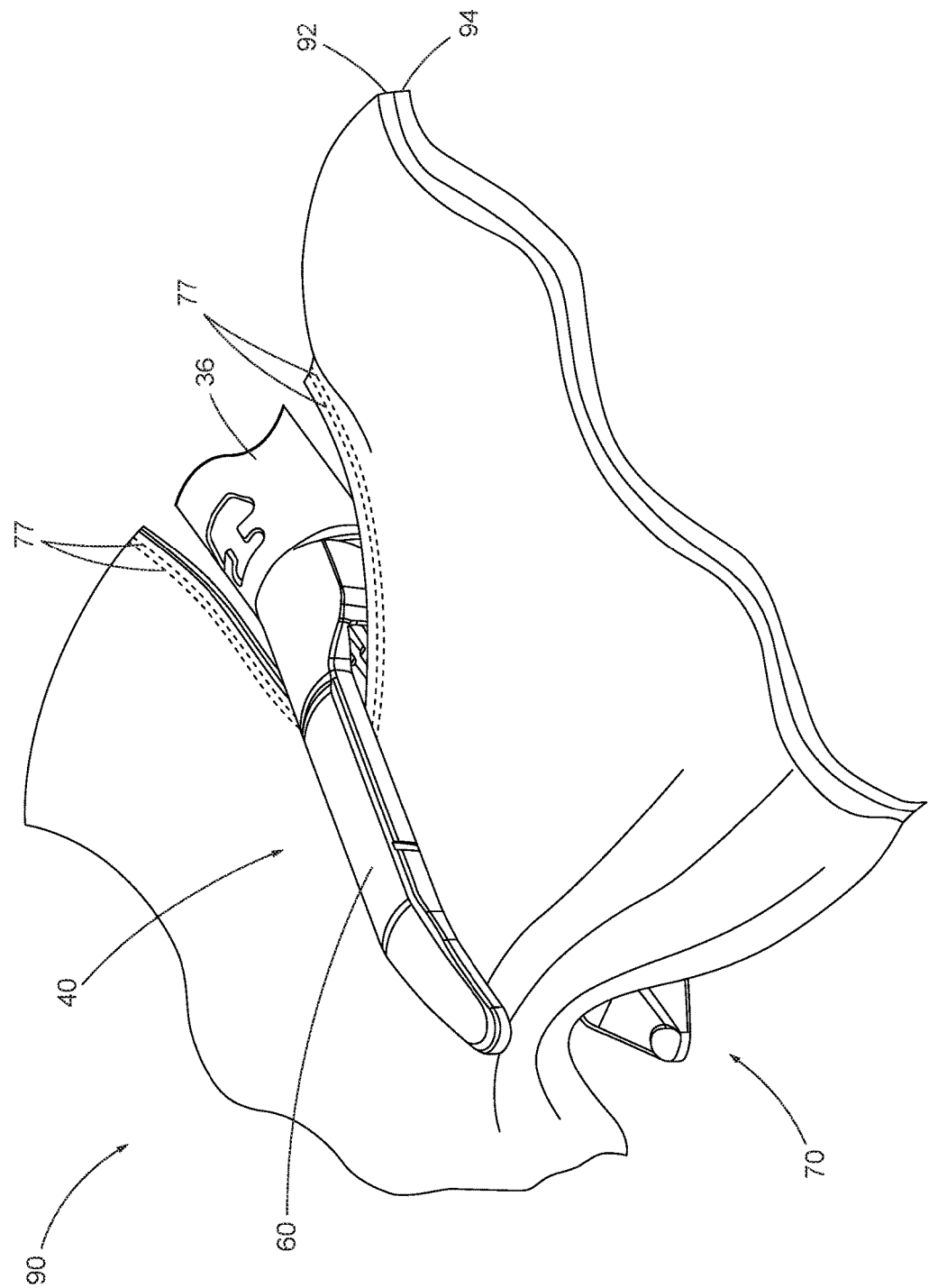
FIG. 8 depicts a perspective view of the end effector of FIG. 3, positioned at tissue and having been actuated once in the tissue.
Figure 9:
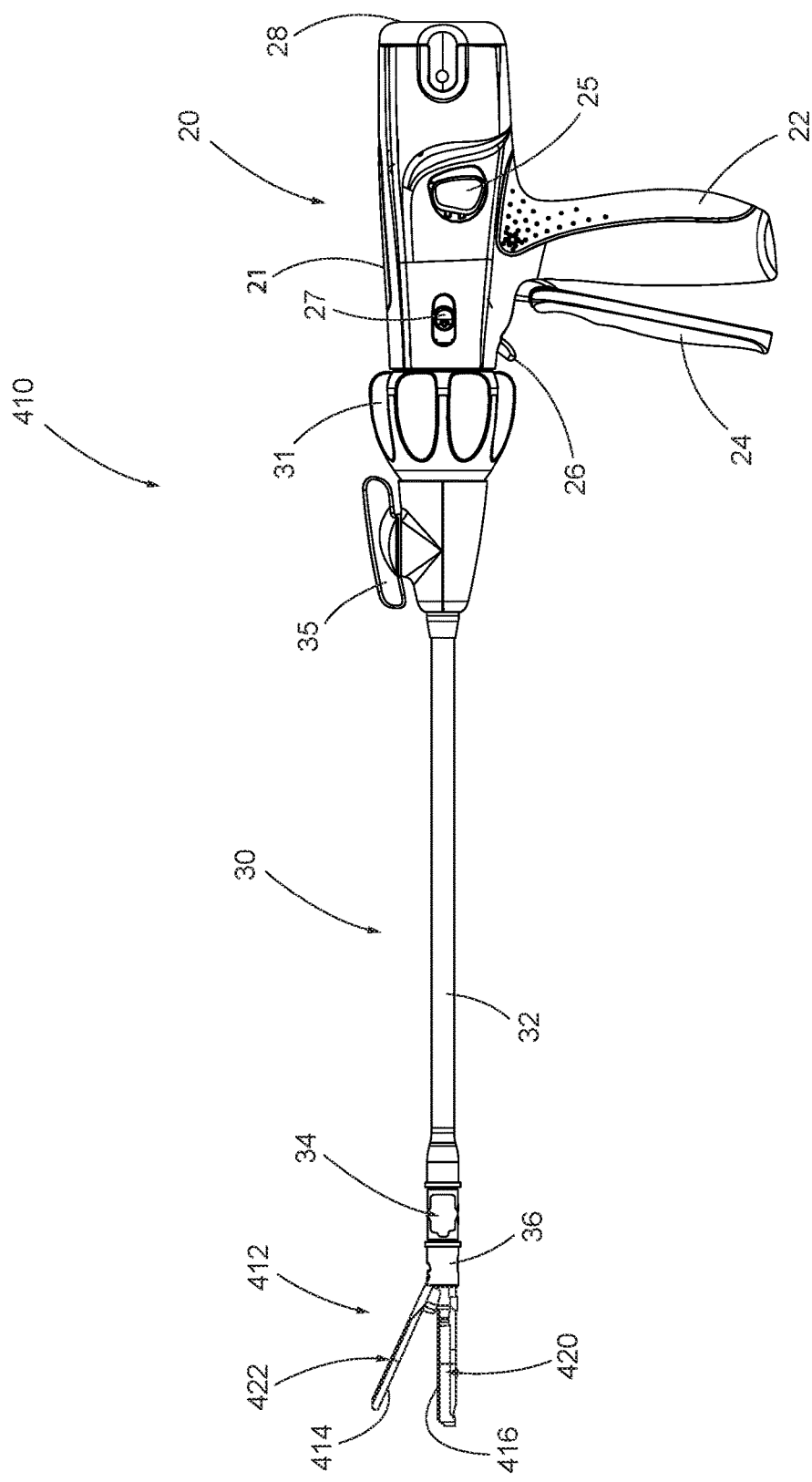
FIG. 9 depicts a side elevational view of still another exemplary articulating surgical stapling instrument.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that staple (77) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Stapling End Effector

While the above surgical instrument (10) provides one example of an end effector (40) that may be used to staple and sever tissue within a patient, it will be appreciated that the human body is comprised a wide variety of tissues located in distinct, sometimes difficult to access regions throughout the patient. For example, a liver includes tissue including vessels or ducts passing throughout. In settings where the liver includes a tumor, it may be desirable to resect the portion of the liver containing the tumor. The resection may be anatomic (e.g., resection of the right or left side of the liver, inclusive of the lobes on that side) or non-anatomic (e.g., resection of just a single lobe or wedge of liver tissue). This resection process may entail at least three kinds of steps—a first step to dissect the tissue (e.g., liver parenchyma) around the vessels or ducts, to thereby isolate or reveal the vessels or ducts; a second step to ligate those vessels or ducts; and a third step to sever the ligated vessels or ducts.

One such method of liver resection includes the well known Kelly clamp method, where a Kelly style clamp is used to compress the liver tissue and thereby dissect the tissue through a crushing action. However, treatments may require many instruments to accommodate such a wide variety of tissues and vessels or ducts within the human body, thereby adding to the time and complexity associated with assessing the state of the tissue, selecting and/or changing instruments, and performing the resection. It may therefore be desirable to provide a surgical instrument (410) with an end effector (412) having a pair of crush surfaces (414, 416) that are configured to sever tissue by crushing the tissue; while also providing an adjacent staple cartridge (418) to selectively ligate one or more vessels or ducts passing through the tissue. Thereby, a single surgical instrument (410) will allow the operator to more quickly assess the tissue and proceed with further tissue dissection and/or ligation of vessels and ducts.

Surrgical instruments (410) are described below in the context of dissecting liver tissue (e.g., liver parenchyma) with crush surfaces (414, 416) and using staples to ligate associated vessels or ducts (e.g., portal vein, hepatic vein branches, hepatic artery branches, extrahepatic vessels, etc.). In some instances (e.g., in the case of hepatic vein branches and hepatic artery branches, etc.), the vessel or duct that is sealed by the staples is exposed when the operator crushes the liver tissue with surfaces (414, 416). In some other instances (e.g., in the case of the portal vein and extrahepatic vessels, etc.), the vessel or duct that is sealed by the staples is separate from the liver tissue that the operator has crushed with surfaces (414, 416). While the following description of surgical instruments (410) and method of treatment is provided in the context of liver resection, it will be appreciated that surgical instruments (410) may be alternatively configured to treat any tissue in the human body with similar features. It should also be understood that that the features discussed below may be readily incorporated into surgical instrument (10) discussed above. To this end, like numbers indicate like features described above in greater detail.

In the following examples, end effectors (412) apply at least two laterally spaced apart rows of staples where the staples in one row have the same height as the staples in another row. In some variations, end effectors (412) are modified to apply at least two laterally spaced apart rows of staples where the staples in one row have a height that is different from the height of the staples in another row.

A. Exemplary Stapling Instrument with Shortened Straight End Effector

FIGS. 9-13 show surgical instrument (410) with end effector (412) having upper crush surface (414), lower crush surface (416), staple cartridge (418), and knife member (419). As noted above, it may be desirable to provide such a surgical instrument (410) with an end effector (412) having crush surfaces (414, 416) that are configured to sever tissue by crushing the tissue; while also providing adjacent staple cartridge (418) to selectively ligate one or more vessels passing through the tissue. In addition, knife member (419) is configured to cut the one or more vessels for complete removal of the surrounding tissue. Thereby, surgical instrument (410) will allow the operator to more quickly assess the tissue and proceed with further tissue severing and/or tissue ligation. Surgical instrument (410) of the present example also includes handle assembly (20) and shaft assembly (30) discussed above in greater detail. Except as otherwise described below, end effector (412), in conjunction with handle assembly (20) and shaft assembly (30), is configured and operable similar to end effector (40) (see FIG. 1). By way of example only, end effector (412) may have a length of approximately 40 mm and a width of approximately 7 mm. Alternatively, any other suitable dimension may be used.

End effector (412) of the present example includes a lower jaw (420) and an upper jaw (422), which forms an anvil (424). Upper jaw (422) is pivotally mounted relative to lower jaw (420) for receiving the tissue therebetween. More particularly, anvil (424) is pivotable toward and away from lower jaw (420) between an open position and a closed position (e.g., in response to pivotal movement of trigger (24) toward and away from pistol grip (22)). For instance, in the present example, anvil (424) pivots about an axis that is defined by pins (not shown), which slide along curved slots (not shown) of lower jaw (420) as anvil (424) moves toward lower jaw (420). In such versions, the pivot axis translates along the path defined by slots (not shown) while anvil (424) simultaneously pivots about that axis. In addition or in the alternative, the pivot axis may slide along slots (not shown) first, with anvil (424) then pivoting about the pivot axis after the pivot axis slides a certain distance along the slots (not shown). Alternatively, some versions may provide pivotal movement of anvil (424) about an axis that remains fixed and does not translate within a slot or channel, etc.

Figure 11:
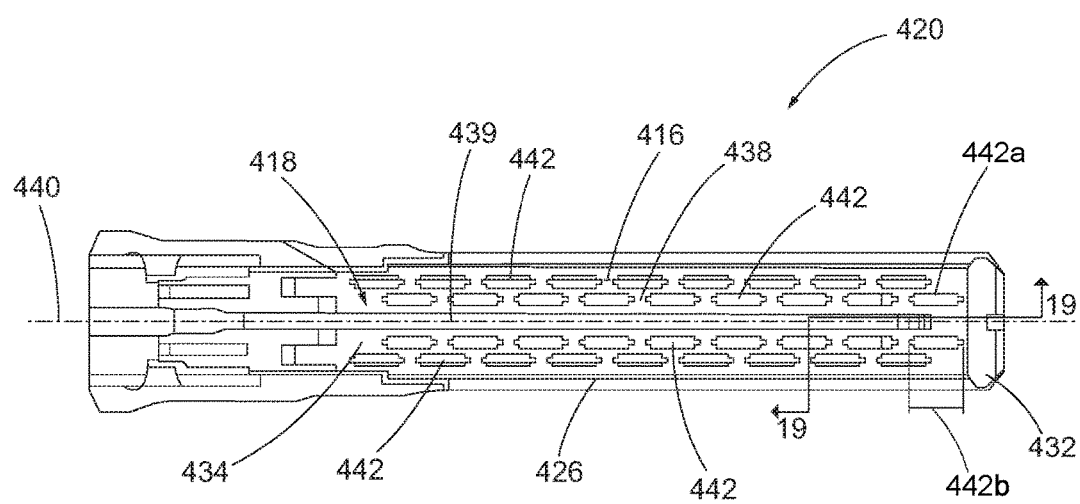
FIG. 11 depicts a top view of a lower jaw of the end effector of FIG. 10.
Figure 12:
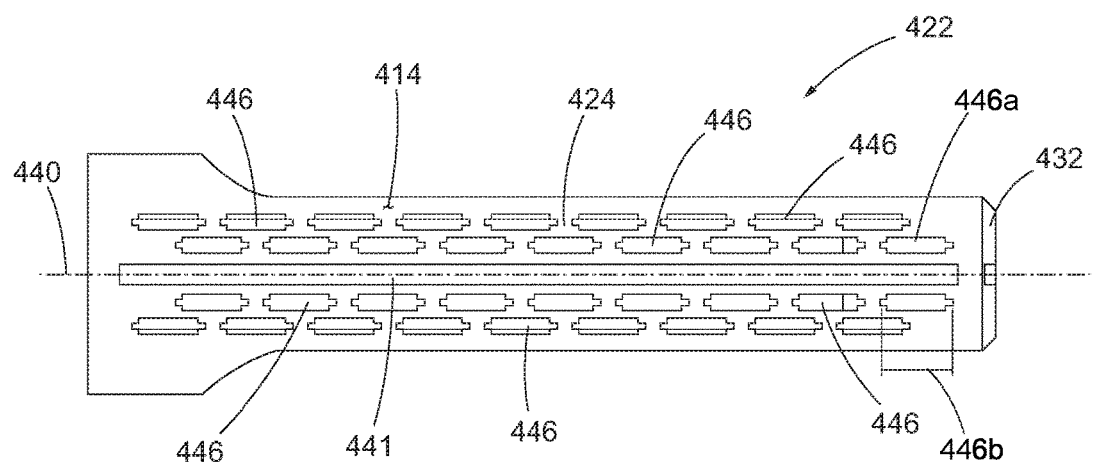
FIG. 12 depicts a bottom view of an upper jaw of the end effector of FIG. 10.
Figure 13:
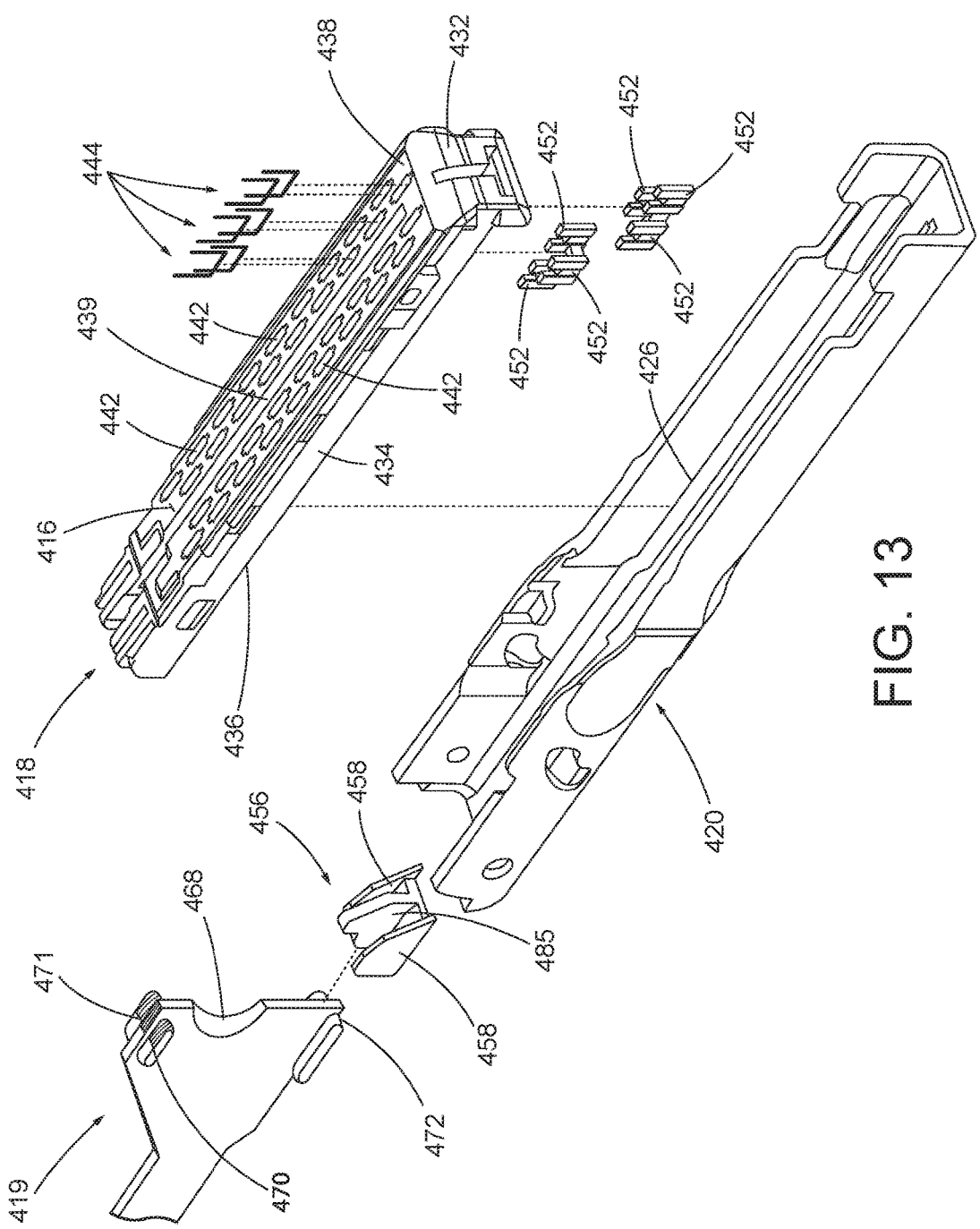
FIG. 13 depicts an exploded perspective view of the lower jaw of FIG. 11.

As best seen in FIGS. 11-13, lower jaw (420) of the present example defines a channel (426) that is configured to receive staple cartridge (418). Staple cartridge (418) may be inserted into channel (426), end effector (412) may be actuated, and then staple cartridge (418) may be removed and replaced with another staple cartridge (418). Lower jaw (420) thus releasably retains staple cartridge (418) in alignment with anvil (424) for actuation of end effector (412). In some alternative versions, the components of staple cartridge (418) are fully integrated into lower jaw (420) such that end effector (412) may only be used once. Other suitable forms that lower jaw (420) may take will be apparent to those of ordinary skill in the art in view of the teachings herein. In the present example, lower and upper jaws (420, 422) extend to a distal tip (432), which is further defined by staple cartridge (418).

Staple cartridge (418) of the present example comprises cartridge body (434) and a tray (not shown) secured to an underside of cartridge body (434). An upper side of cartridge body (434) presents a deck (438), against which tissue may be compressed when anvil (424) is in a closed position. In the present example, lower crush surface (416) is positioned along staple cartridge (418). However, it will be appreciated that lower crush surface (416), as well as cooperating upper crush surface (414) may be alternatively positioned along end effector (412) for severing tissue via compression.

Cartridge body (434) further defines an elongated channel (439) extending through lower jaw (420) and linearly along a centerline (440) of end effector (412). Another elongated channel (441) defined by anvil (424) extends through upper jaw (422) and linearly along centerline (440), as well, for reasons discussed below in greater detail. A plurality of staple pockets (442) follow a predetermined pattern along deck (438) on opposing sides of centerline (440) to a pair of distal-most staple pockets (442a), which each respectively define a longitudinal cartridge pocket length (442b). More particularly, staple cartridge (418) includes two longitudinally extending rows of staple pockets (442) on one side of centerline (440); and another set of two longitudinally extending rows of staple pockets (442) on the other side of centerline (440). However, in some other versions, staple cartridge (418) may include three, one, or some other number of staple pockets (442) on each side of centerline (440).

One of a plurality of staples (444) is positioned in respective staple pockets (442). Adjacent rows of staple pockets (442) are configured to overlap in a direction transverse to the centerline (440) in order to install the plurality of staples (444) within the tissue and inhibit openings therebetween for improved ligation. In other words, a consistent gap (G1) is maintained between adjacent staple pockets (442) for consistent overlap in the present example. As used herein, the term "overlap" is intended to include one feature overlapping with another in at least one direction. Thus, a feature may be offset from another feature and still overlap as described herein in the event that these features overlap in at least one plane, such as a transverse plane including the transverse direction. Other suitable forms that staple cartridge (418) may take will be apparent to those of ordinary skill in the art in view of the teachings herein.

With respect to FIGS. 11-13, anvil (424) of the present example has a plurality of staple forming pockets (446), including a pair of distal-most staple forming pockets (446a), which each respectively define a longitudinal anvil pocket length (446b). Each staple forming pocket (446) is positioned to lie over a corresponding staple pocket (442) of staple cartridge (418) when anvil (424) is in a closed position. Staple forming pockets (446) are configured to deform each leg (448) of staples (444) when staples (444) are driven through tissue and into anvil (424). In particular, staple forming pockets (446) are configured to bend legs (448) of staples (444) to secure the formed staples (444) in the tissue. Other suitable forms that anvil (424) may take will be apparent to those of ordinary skill in the art in view of the teachings herein.

As best seen in FIG. 13, staple cartridge (418) includes staple drivers (452) positioned in staple pockets (442), underneath a corresponding staple (444), and above tray (not shown). As will be described in greater detail below, staple drivers (452) are operable to translate upwardly in staple pockets (442) to thereby drive staples (444) upwardly through staple pockets (442) and into engagement with anvil (424). Staple drivers (452) are driven upwardly by a wedge sled (456), which is captured between cartridge body (434) and tray (not shown), and which translates longitudinally through cartridge body (434) along a pair of cam slots (457).

Wedge sled (456) includes a cam ramp (258) having a leading cam surface (460), an intermediate cam surface (462), and a trailing cam surface (464). By way of example only, leading cam surface (460) may be angled at approximately 45° relative to a horizontal plane; and intermediate cam surface (462) may be angled at approximately 22° relative to a horizontal plane. Alternatively, any other suitable angles may be used. Cam ramps (458) are generally configured to engage staple drivers (452) and thereby drive staple drivers (452) upwardly as wedge sled (456) translates longitudinally through staple cartridge (418) from a proximal sled position to a distal sled position. For instance, when wedge sled (456) is in the proximal sled position, staple drivers (452) are in downward positions and staples (444) are located in staple pockets (442). As wedge sled (456) is driven to the distal sled position by translating knife member (419), wedge sled (456) drives staple drivers (452) upwardly, thereby driving staples (444) out of staple pockets (442) and into staple forming pockets (446). Thus, staple drivers (452) translate along respective vertical planes as wedge sled (456) translates along a horizontal plane.

In the present example, knife member (419) is configured to translate through end effector (412). As best seen in FIG. 13, knife member (419) is secured to a distal end of firing beam (82), which extends through a portion of shaft assembly (30). Knife member (80) is positioned in channels (439, 441) of staple cartridge (418) and anvil (424), respectively. Knife member (419) includes a distally presented cutting edge (468) that is configured to sever tissue that is compressed between anvil (424) and deck (438) of staple cartridge (418) as knife member (419) translates distally through end effector (412). As noted above, knife member (419) also drives wedge sled (456) distally as knife member (419) translates distally through end effector (412), thereby driving staples (444) through tissue and against anvil (424) into formation.

1. Exemplary Upper and Lower Staple Usage Indicia of End Effector

Figure 14:
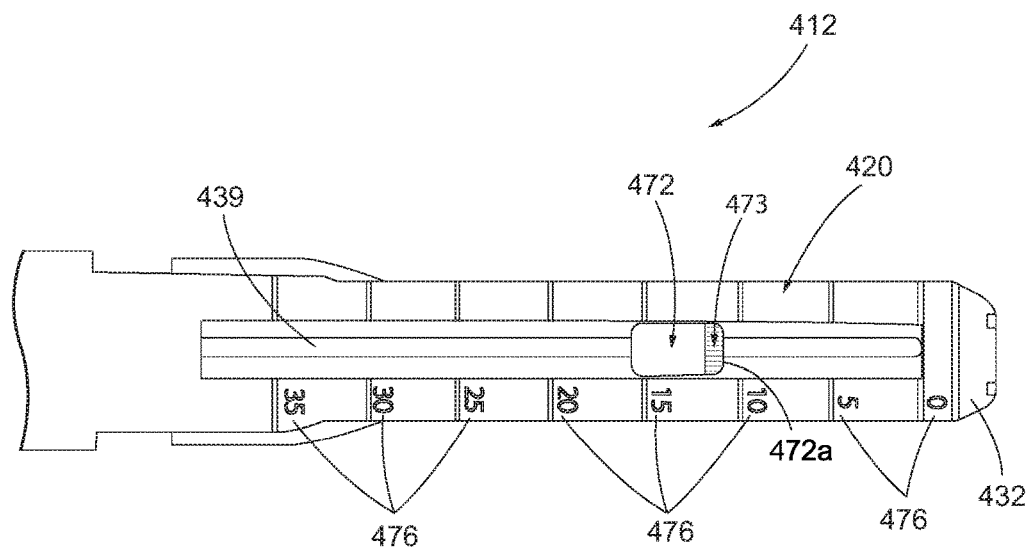
FIG. 14 depicts a bottom view of the end effector of FIG. 10.
Figure 15:
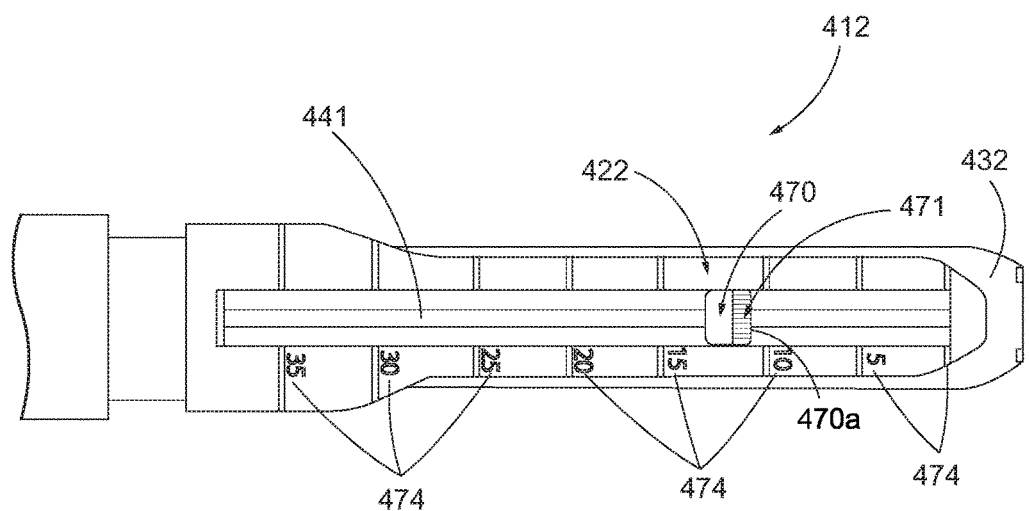
FIG. 15 depicts a top view of the end effector of FIG. 10.

As shown in FIGS. 14-15, lower and upper jaws (420, 422) have elongated channels (439, 441) extending through anvil (424) and staple cartridge (434), respectively. As discussed herein in greater detail, elongated channel (439) receives translating knife member (419) that is configured to push wedge sled (456) from the proximal position to the distal position for selectively forming staples (444) in the tissue of the patient. In addition, knife member (419) includes an upper flange (470) having an upper distal flange edge (470a) and a lower flange (472) having a lower distal flange edge (472a) that respectively project from channels (441, 439). Flanges (470, 472) extend transversely from the vertical plane defined by knife member (419). Upper flange (470) is configured to bear downwardly on the top side of upper jaw (422) as knife member (419) translates through end effector (412); and lower flange (472) is configured to bear upwardly on the bottom side of lower jaw (420) as knife member (419) translates through end effector (412). Flanges (470, 472) may thus cooperate to enhance compression that is already being applied by jaws (420, 422) as knife member (419) translates through end effector (412).

Knife member (419) further includes markings (471, 473) that are on and/or near flanges (470, 472). Markings (471, 473) are positioned such that markings (471) may be readily viewed by the user. Markings (471, 473) are configured to provide the operator with a visual indication of the longitudinal position of cutting edge (468), which may further indicate the location of the cut line in tissue. In some versions, the longitudinal position of cutting edge (468) is proximal to the longitudinal position of the distal edges of flanges (470, 472). Markings (471, 473) may thus provide the operator with enhanced visual feedback that is more useful than the visual feedback that would otherwise be provided through observation of the distal edges of flanges (470, 472) during translation of knife member (419). It should also be understood that markings (471, 473) may enable immediate visualization of the location of knife member (419) within end effector (412) from either the top or bottom view during use.

Figure 10:
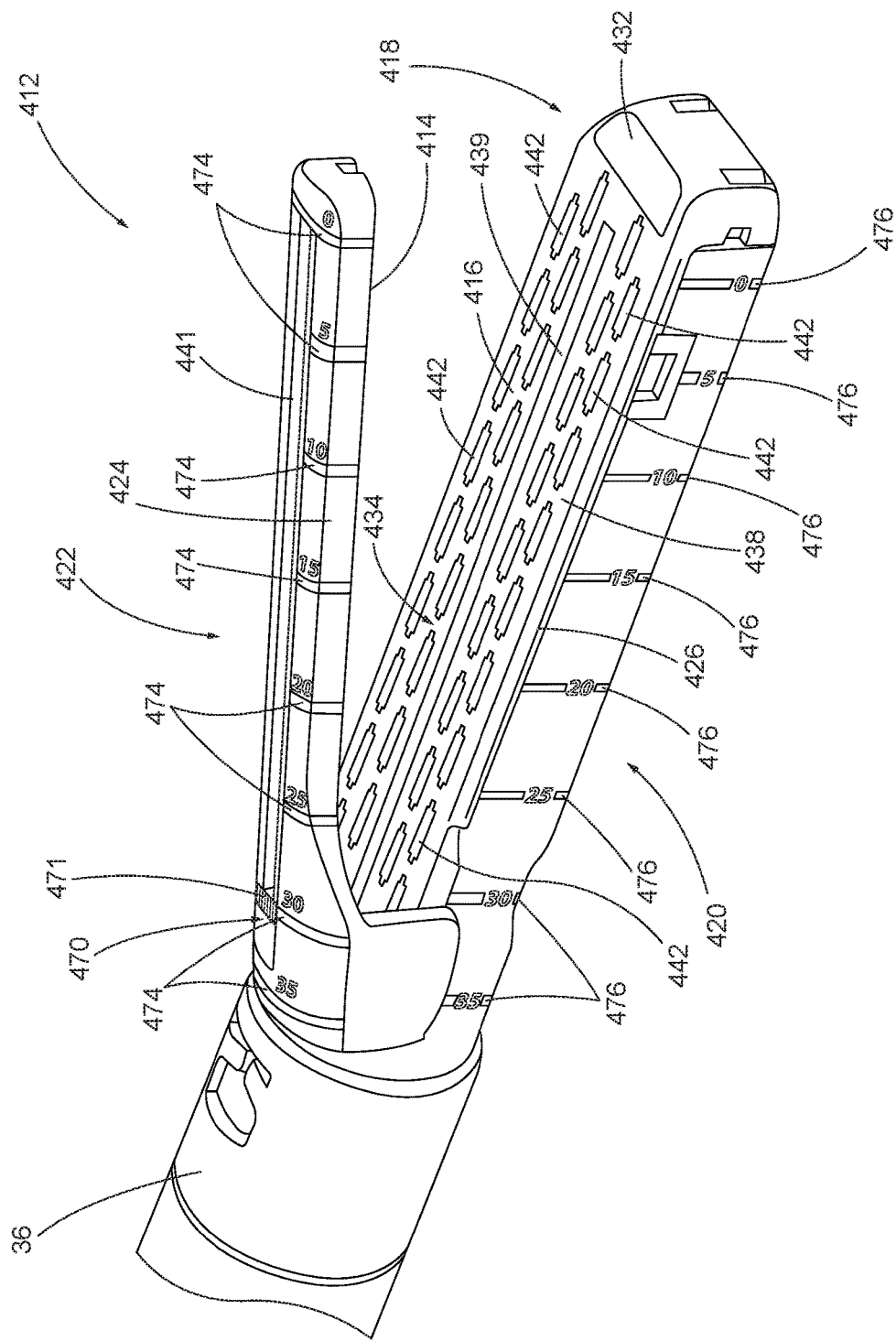
FIG. 10 depicts a perspective view of an end effector of the instrument of FIG. 9, with the end effector in an open configuration.

Furthermore, upper and lower jaws (422, 420) also include a plurality of upper indicia (474) and a plurality of lower indicia (476), respectively. As shown in FIGS. 10 and 15, upper indicia (474) are visible from the top of end effector (412) and from the sides of end effector (412). As shown in FIGS. 10 and 14, lower indicia (476) are visible from the bottom of end effector (412) and from the sides of end effector (412). Each upper indicia (474) is more particularly configured to indicate a remaining amount of staples (444) positioned distally from each respective upper indicia (474). Similarly, each lower indicia (476) is configured to indicate the remaining amount of staples (444) positioned distally from each respective lower indicia (476). In other words, the upper and lower indicia (474, 476) each provide usage indicia of staples (444). Thereby, upper and/or lower indicia (474, 476) in combination with markings (471, 473) are configured to indicate to the operator the remaining amount of staples (444) within staple cartridge (418) in real time during use. The operator may thus view the upper and lower usage indicia (474, 476) more effectively from the top or bottom views and, in turn, more effectively use remaining staples (444) during tissue resection.

In some versions, upper and lower usage indicia (474, 476) includes a countdown of remaining staples that extends distally, from "35" staples (444) at the proximal end to "0" staples at distal tip (432), in increments of five. Alternatively, any other suitable indicia configured to indicate usage may be so used. It will be appreciated that upper and lower usage indicia (474, 476) may also comprise an accumulation of used staples (444), such that upper and lower usage indicia (474, 476) indicate the number of staples (444) used rather than the number of staples (444) remaining in staple cartridge (418). As such, the term "usage indicia" is intended to be used broadly, rather than limit the invention to a particular countdown or accumulation of staples (444).

2. Exemplary Method of Tissue Resection

FIGS. 16A-16E show one example of using end effector (412) to resect tissue, such as a liver parenchyma tissue (310), and to ligate a vessel or duct (316) therein. As noted above, vessel or duct (316) may comprise a hepatic vein or a hepatic artery. It should also be understood that the method may further include the use of end effector (412) to ligate other vessels such as the portal vein and extrahepatic vessels, etc.

Figure 16A:
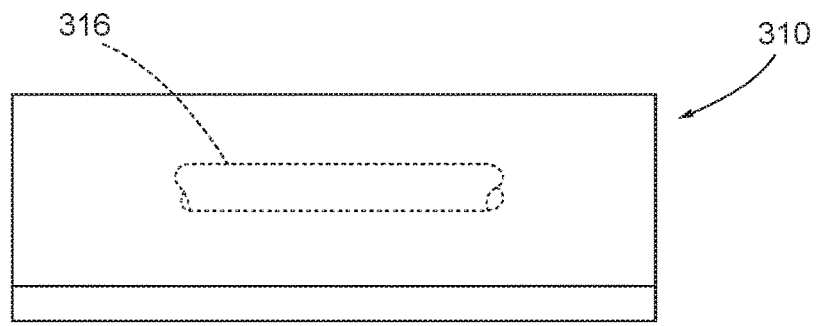
FIG. 16A depicts a schematic representation of a liver having a vessel extending through the liver tissue.
Figure 16B:
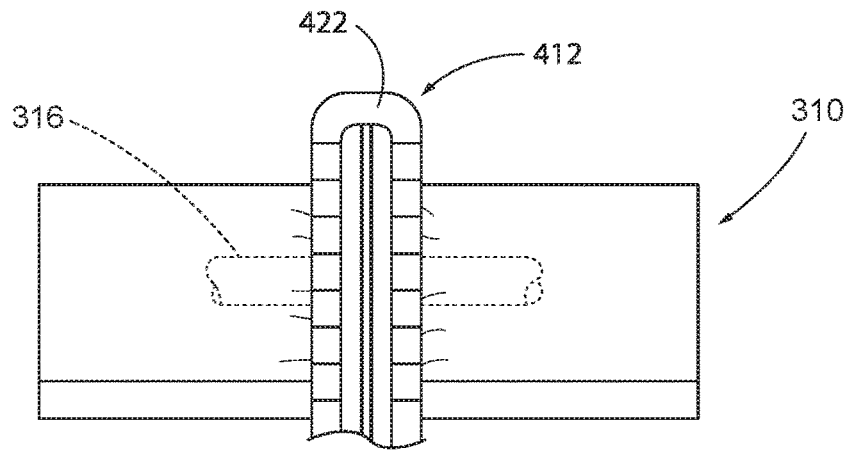
FIG. 16B depicts the schematic representation of the end effector of FIG. 10 severing the liver tissue of FIG. 16A.

As shown in FIG. 16B, the operator positions end effector (412) such that tissue (310), including vessel or duct (316), is located between lower and upper jaws (420, 422). The operator then compresses tissue (310) between upper and lower crush surfaces (414, 416) of upper and lower jaws (420, 422), respectively, to deliver the predetermined crush pressure to tissue (310). By way of example only, jaws (420, 422) may be actuated in this manner by pivoting trigger (24) toward pistol grip (22). It should be understood that jaws (420, 422) need not necessarily be actuated to a fully closed configuration. In some instances, the operator may rely on tactile feedback through trigger (24) and pistol grip (22) to determine whether the operator has achieved a desired gap between jaws (420, 422) to suitably crush tissue (310) without undesirably damaging vessel or duct (316). In addition or in the alternative, the operator may rely on visual feedback.

Figure 16C:
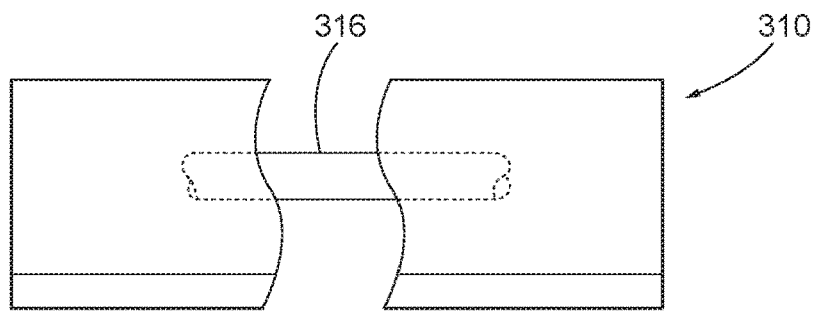
FIG. 16C depicts the schematic representation of the vessel of FIG. 16B exposed from the severed liver tissue of FIG. 16A.

In any case, the crush pressure applied by jaws (420, 422) effectively severs tissue (310), and the operator then removes end effector (412) from tissue (310) to view whether or not any vessels or ducts are present. As shown in FIG. 16C, vessel or duct (316) remains intact and is left exposed, extending between severed portions of tissue (310).

Figure 16D:
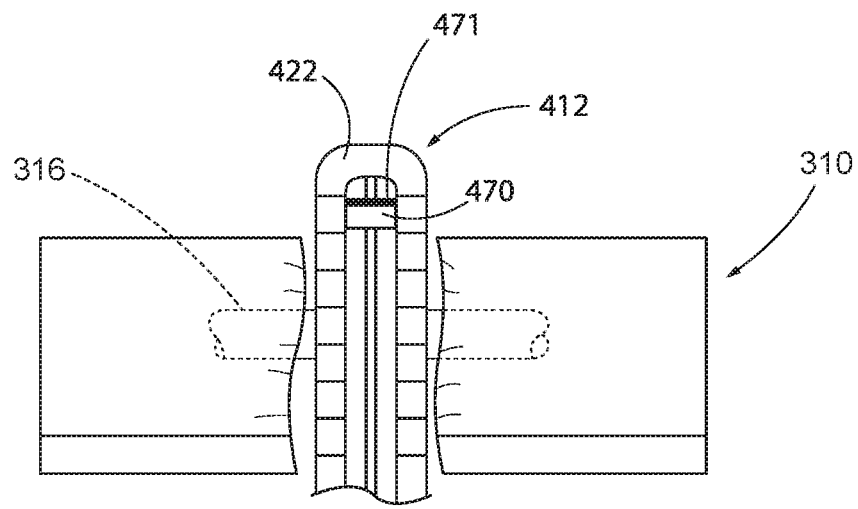
FIG. 16D depicts the schematic representation of the end effector of FIG. 10 stapling the exposed vessel of FIG. 16C.
Figure 16E:
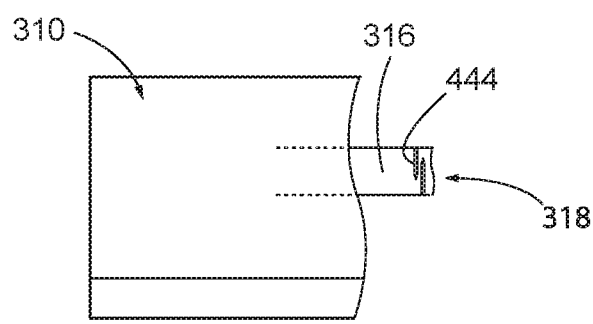
FIG. 16E depicts the schematic representation of the liver of FIG. 16A having a portion of the liver tissue and the vessel resected therefrom.

In some instances, the operator may leave vessel or duct (316) intact. However, in the present example, the operator ligates vessel or duct (316) to complete the resection of a severed portion of tissue (310), as shown in FIG. 16D. Ligation includes placement of at least some of overlapping staples (444) within vessel or duct (316) as discussed above in greater detail. It should therefore be understood that the same end effector (412) may be used to crush (and thereby sever) tissue (310) of the liver and also ligate a vessel or duct (316) in the tissue (310). In the present example, the vessel or duct (316) is stapled and severed substantially simultaneously by end effector (412), resulting in the configuration shown in FIG. 16E. As shown, the severed end (318) of the vessel or duct (316) is sealed by staples (444). Thereby, the operator completes resection of a right portion of tissue (310) and the corresponding portion of the vessel or duct (316).

As described above, the operator removes end effector (412) for viewing vessel (316) as shown in FIG. 16C. Alternatively, the operator may apply the predetermined crush pressure (or as determined based on tactile and/or visual feedback as noted above), as shown in FIG. 16B, and immediately thereafter sever and ligate any tissue remaining therein, such as vessel or duct (316). As such, it is not necessary to view such tissue, but the operator may find such viewing desirable in one or more liver resection procedures. It will be appreciated that the above described resection is merely illustrative and not limited to liver tissue. Alternatively, tissue resection with end effector (412) may be performed on other tissues within the patient as desired by the user.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument for treating a tissue of a patient, comprising: (a) a shaft assembly; and (b) an end effector extending from the shaft assembly along a jaw centerline, the end effector comprising: (i) a first jaw, wherein the first jaw comprises: (A) an anvil configured to form a plurality of staples pressed thereagainst, (B) an upper elongated channel extending therethrough, and (C) a first plurality of indicia positioned proximate to the first elongated channel, (ii) a second jaw, wherein the first and second jaws are configured to transition between an open configuration and a closed configuration, wherein the second jaw comprises: (A) a second elongated channel extending therethrough, and (B) a second plurality of indicia positioned proximate to the second elongated channel, and (iii) a translating member received within the first and second channels, wherein the translating member is configured to slide distally along the first and second channels and engage the wedge sled for forming staples, wherein the translating member comprises a first indicator and a second indicator, wherein the first and second indicators in conjunction with the first and lower plurality of indicia are respectively configured to indicate one or both of staple usage or a cut position to an operator.

EXAMPLE 2

The surgical instrument of Example 1, wherein the indicated staple usage represents an amount of the plurality of staples remaining in the staple cartridge.

EXAMPLE 3

The surgical instrument of any one or more of Examples 1 through 2, wherein the plurality of first indicia is in the form of a numerical countdown extending distally along the first jaw, and wherein the plurality of second indicia is in the form of another numerical countdown extending distally along the second jaw.

EXAMPLE 4

The surgical instrument of any one or more of Examples 1 through 3, further comprising a staple cartridge received within the second jaw.

EXAMPLE 5

The surgical instrument of any one or more of Examples 1 through 4, wherein the translating member is in the form of a knife member configured to cut the tissue.

EXAMPLE 6

The surgical instrument of any one or more of Examples 1 through 5, wherein the translating member comprises a first flange and a second flange, wherein the first flange extends through the first elongated channel and is engaged with the first jaw, wherein the second flange extends through the second elongated channel and engages the second jaw.

EXAMPLE 7

The surgical instrument of Example 6, wherein the first indicator is on the first flange, wherein the second indicator is on the second flange.

EXAMPLE 8

The surgical instrument of any one or more of Examples 1 through 7, wherein the first and second elongated channels extend parallel to the centerline.

EXAMPLE 9

The surgical instrument of Example 8, wherein the first elongated channel extends along the centerline.

EXAMPLE 10

The surgical instrument of Example 9, wherein the second channel extends along the centerline.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,749,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument for treating a tissue of a patient, comprising:
    (a) a shaft assembly; and
    (b) an end effector extending from the shaft assembly along a longitudinally extending jaw centerline, the end effector comprising:
        (i) a first jaw, wherein the first jaw comprises:
            (A) an anvil extending to a distal-most anvil end and having a plurality of staple forming pockets configured to respectively form a plurality of staples pressed thereagainst, wherein the plurality of staple forming pockets includes a distal-most staple forming pocket defining a longitudinal anvil pocket length, wherein the distal-most anvil end of the first jaw is distally positioned less than the longitudinal anvil pocket length from the distal-most staple forming pocket,
            (B) a first elongated channel extending therethrough, and
            (C) a first plurality of indicia positioned proximate to the first elongated channel,
        (ii) a second jaw, wherein the first and second jaws are configured to transition between an open configuration and a closed configuration, wherein the second jaw comprises:
            (A) a second elongated channel extending therethrough, and
            (B) a second plurality of indicia positioned proximate to the second elongated channel, and
        (iii) a knife member received within the first and second elongated channels and having a distal cutting edge configured to cut tissue, wherein the knife member is configured to slide longitudinally and distally along the first and second elongated channels and engage a wedge sled for forming staples, wherein the knife member comprises:

(A) a first distal end portion of the knife member projecting beyond the first elongated channel,
(B) a second distal end portion of the knife member positioned transversely opposite from the first distal end portion and projecting beyond the second elongated channel,
(C) a first flange laterally extending from the first distal end portion of the knife member and configured to transversely overlap the first jaw, wherein the first flange includes a first distal flange edge,
(D) a second flange laterally extending from the second distal end portion of the knife member and configured to transversely overlap the second jaw, wherein the second flange includes a second distal flange edge, and
(E) a first indicator and a second indicator, wherein the first and second indicators in conjunction with the first and second plurality of indicia are respectively configured to indicate one or both of staple usage or a cut position to an operator, wherein the first and second indicators transversely align with the distal cutting edge in a transverse plane that perpendicularly intersects the jaw centerline such that the first and second indicators are each configured to indicate the cut position to the operator, and wherein the first indicator is on the first flange extending to the first distal flange edge, and wherein the second indicator is on the second flange extending to the second distal flange edge.

2. The surgical instrument of claim 1, wherein the first and second indicators in conjunction with the first and second plurality of indicia are respectively further configured to indicate staple usage.

3. The surgical instrument of claim 1, wherein the plurality of first indicia is in the form of a numerical countdown extending distally along the first jaw, and wherein the plurality of second indicia is in the form of another numerical countdown extending distally along the second jaw.

4. The surgical instrument of claim 1, further comprising a staple cartridge received within the second jaw and extending to a distal-most cartridge end, wherein the staple cartridge has a plurality of staple pockets respectively containing a plurality of staples therein, wherein the plurality of staple pockets includes a distal-most staple pocket defining a longitudinal cartridge pocket length, wherein the distal-most cartridge end of the staple cartridge is distally positioned less than the longitudinal cartridge pocket length from the distal-most staple pocket.

5. The surgical instrument of claim 1, wherein the first flange is configured to transversely engage the first jaw and direct the first jaw transversely toward the second jaw, wherein the second flange is configured to transversely engage the second jaw and direct the second jaw transversely toward the first jaw.

6. The surgical instrument of claim 1, wherein the first and second elongated channels extend parallel to the centerline.

7. The surgical instrument of claim 6, wherein the first elongated channel extends along the centerline.

8. The surgical instrument of claim 2, wherein the indicated staple usage represents an amount of the plurality of staples remaining in the staple cartridge.

9. The surgical instrument of claim 1, wherein the end effector further includes a first elongated flange channel extending along the first jaw adjacent to the first elongated channel, wherein the first elongated flange channel is configured to at least partially receive the first flange therein.

10. The surgical instrument of claim 9, wherein the end effector further includes a second elongated flange channel extending along the second jaw adjacent to the second elongated channel, wherein the second elongated flange channel is configured to at least partially receive the second flange therein.

11. The surgical instrument of claim 1, wherein the first plurality of indicia includes a distal-most indicia on the first jaw, and wherein the distal-most anvil end of the first jaw is distally positioned less than the longitudinal anvil pocket length from the distal-most indicia.

12. The surgical instrument of claim 1, wherein the knife member is configured to slide distally from a proximal position to a distal-most position, and wherein each of the first and second indicators in the distal-most position is positioned less than the longitudinal pocket length from the distal-most staple forming pocket.

13. A surgical instrument for treating a tissue of a patient, comprising:
(a) a shaft assembly; and
(b) an end effector longitudinally extending from the shaft assembly along a jaw centerline, the end effector comprising:
(i) a first jaw, wherein the first jaw comprises:
(A) an anvil configured to form a plurality of staples pressed thereagainst, and
(B) a first elongated channel extending therethrough,
(ii) a second jaw, wherein the first and second jaws are configured to transition between an open configuration and a closed configuration, wherein the second jaw comprises:
(A) a second elongated channel extending therethrough, and
(B) a staple cartridge received within the second jaw and longitudinally extending to a distal-most cartridge end, wherein the staple cartridge has a plurality of staple pockets respectively containing a plurality of staples therein, wherein the plurality of staple pockets includes a distal-most staple pocket defining a longitudinal cartridge pocket length, and wherein the distal-most cartridge end of the staple cartridge is distally positioned less than the longitudinal cartridge pocket length from the distal-most staple pocket, and
(iii) a knife member received within the first and second elongated channels, along the first and second elongated channels and engage a wedge sled for forming staples, wherein the knife member comprises:
(A) a distal cutting edge configured to cut the tissue, and
(B) a first indicator and a second indicator, wherein the first and second indicators transversely align with the distal cutting edge in a transverse plane that perpendicularly intersects the jaw centerline such that the first and second indicators are each configured to indicate a cut position to an operator.

14. The surgical instrument of claim 13, wherein the first jaw further includes a first plurality of indicia positioned proximate to the first elongated channel, and wherein the second jaw further includes a second plurality of indicia positioned proximate to the second elongated channel.

15. The surgical instrument of claim 14, wherein the first and second indicators in conjunction with the first and second plurality of indicia are respectively further configured to indicate staple usage.

16. The surgical instrument of claim 13, wherein the knife member is configured to slide distally from a proximal position to a distal-most position, wherein the anvil further extends to a distal-most end and has a plurality of staple forming pockets configured to respectively form the plurality of staples pressed thereagainst, wherein the plurality of staple forming pockets includes a distal-most staple forming pocket defining a longitudinal pocket length, wherein the distal-most end of the first jaw is distally positioned less than the longitudinal pocket length from the distal-most staple forming pocket, and wherein each of the first and second indicators in the distal-most position is positioned less than the longitudinal pocket length from the distal-most staple forming pocket.

17. The surgical instrument of claim 16, wherein the first jaw further includes a first plurality of indicia positioned proximate to the first elongated channel, wherein the first plurality of indicia includes a distal-most indicia on the first jaw, and wherein the distal-most anvil end of the first jaw is distally positioned less than the longitudinal pocket length from the distal-most indicia.

18. A surgical instrument for treating a tissue of a patient, comprising:
(a) a shaft assembly; and
(b) an end effector longitudinally extending from the shaft assembly along a jaw centerline, the end effector comprising:
  (i) a first jaw, wherein the first jaw comprises:
    (A) an anvil configured to form a plurality of staples pressed thereagainst, and
    (B) a first elongated channel extending therethrough,
  (ii) a second jaw, wherein the first and second jaws are configured to transition between an open configuration and a closed configuration, wherein the second jaw comprises:
    (A) a second elongated channel extending therethrough, and
  (iii) a knife member received within the first and second elongated channels, along the first and second elongated channels and engage a wedge sled for forming staples, wherein the knife member comprises:
    (A) a distal cutting edge configured to cut the tissue, and
    (B) a first indicator and a second indicator, wherein the first and second indicators transversely align with the distal cutting edge in a transverse plane that perpendicularly intersects the jaw centerline such that the first and second indicators are each configured to indicate a cut position to an operator,
  wherein the knife member is configured to slide distally from a proximal position to a distal-most position, wherein the anvil further longitudinally extends to a distal-most end and has a plurality of staple forming pockets configured to respectively form the plurality of staples pressed thereagainst, wherein the plurality of staple forming pockets includes a distal-most staple forming pocket defining a longitudinal pocket length, wherein the distal-most end of the first jaw is distally positioned less than the longitudinal pocket length from the distal-most staple forming pocket, and wherein each of the first and second indicators in the distal-most position is positioned less than the longitudinal pocket length from the distal-most staple forming pocket.

19. The surgical instrument of claim 18, further comprising a staple cartridge received within the second jaw and extending to a distal-most cartridge end, wherein the staple cartridge has a plurality of staple pockets respectively containing a plurality of staples therein, wherein the plurality of staple pockets includes a distal-most staple pocket defining a longitudinal cartridge pocket length, and wherein the distal-most cartridge end of the staple cartridge is distally positioned less than the longitudinal cartridge pocket length from the distal-most staple pocket.

20. The surgical instrument of claim 19, wherein the second jaw further includes a plurality of indicia positioned proximate to the first elongated channel, wherein the plurality of indicia includes a distal-most indicia on the second jaw, and wherein the distal-most cartridge end is distally positioned less than the longitudinal cartridge pocket length from the distal-most indicia.

* * * * *